(12) United States Patent
Himeda et al.

(10) Patent No.: US 7,514,097 B1
(45) Date of Patent: *Apr. 7, 2009

(54) USE OF SOLUBLE CELLULOSE DERIVATIVE HAVING BEEN MADE HARDLY SOLUBLE IN WATER AND PROCESS FOR PRODUCING THE SAME

(75) Inventors: Yasukazu Himeda, Tokyo (JP); Toshihiko Umeda, Tokyo (JP)

(73) Assignee: Denki Kagaku Kogyo Kabushiki Kaisha, Tokyo (JP)

( * ) Notice: Subject to any disclaimer, the term of this patent is extended or adjusted under 35 U.S.C. 154(b) by 447 days.

This patent is subject to a terminal disclaimer.

(21) Appl. No.: 10/129,751

(22) PCT Filed: Aug. 18, 2000

(86) PCT No.: PCT/JP00/05564

§ 371 (c)(1),
(2), (4) Date: May 9, 2002

(87) PCT Pub. No.: WO01/34214

PCT Pub. Date: May 17, 2001

(30) Foreign Application Priority Data

Nov. 9, 1999 (JP) .............................. 11-318587
Feb. 17, 2000 (JP) .............................. 2000-039244

(51) Int. Cl.
*A61K 31/715* (2006.01)
*A61K 31/075* (2006.01)
*A61L 15/16* (2006.01)
*A61L 15/00* (2006.01)
*A01N 43/04* (2006.01)
*A01N 31/14* (2006.01)

(52) U.S. Cl. .......................... 424/444; 514/54; 514/57; 514/718; 424/445

(58) Field of Classification Search ................. 424/400, 424/443, 449, 422, 423, 424, 445, 781; 514/23, 514/54, 57, 444; 623/66.1
See application file for complete search history.

(56) References Cited

U.S. PATENT DOCUMENTS

| | | | |
|---|---|---|---|
| 261,780 A | | 7/1882 | Stevens |
| 2,617,800 A | | 11/1952 | Bergman .................... 260/232 |
| 3,064,313 A | * | 11/1962 | Butler ........................ 264/187 |
| 4,256,877 A | * | 3/1981 | Karlsson et al. ............... 536/59 |
| 4,521,594 A | | 6/1985 | Kanematu |
| 4,851,010 A | * | 7/1989 | Coleman-Kammula et al. ........................ 8/115.62 |
| 5,017,229 A | * | 5/1991 | Burns et al. .............. 106/162.2 |
| 5,466,461 A | | 11/1995 | Della Valle et al. |
| 5,676,964 A | | 10/1997 | Della Valle et al. |
| 5,705,485 A | | 1/1998 | Cini et al. ..................... 514/12 |
| 5,760,200 A | | 6/1998 | Miller et al. ................... 536/21 |
| 5,888,987 A | | 3/1999 | Haynes et al. ................. 514/54 |
| 5,906,997 A | * | 5/1999 | Schwartz et al. ............ 514/781 |
| 6,638,538 B1 | * | 10/2003 | Hashimoto et al. .......... 424/548 |

FOREIGN PATENT DOCUMENTS

| | | |
|---|---|---|
| DE | 1397893 | 11/1934 |
| EP | 47647 | 3/1982 |
| EP | 0341745 A1 | 11/1989 |
| EP | 0614914 A2 | 9/1994 |
| EP | 705878 | 4/1996 |
| GB | 1042864 | 9/1966 |
| GB | 1086323 | 10/1967 |
| JP | 62-39506 | 2/1987 |
| JP | 62-183768 | 8/1987 |
| JP | 63-37143 | 2/1988 |
| JP | 1-301624 | 12/1989 |
| JP | 3-23864 | 1/1991 |
| JP | 5-508161 | 11/1993 |
| JP | 6-508169 | 9/1994 |
| JP | 7-90121 | 4/1995 |
| JP | 7-109220 | 4/1995 |
| JP | 7-505643 | 6/1995 |
| JP | 7-179649 | 7/1995 |
| JP | 8-505258 | 6/1996 |
| JP | 10-251447 | 9/1998 |
| JP | 11-106561 | 4/1999 |
| JP | 11-322615 | 11/1999 |
| JP | 2000-178304 | 6/2000 |
| NZ | 232434 | 2/1992 |
| NZ | 259734 | 7/1997 |
| NZ | 332112 | 6/2000 |
| WO | WO 80/00842 | 5/1980 |
| WO | WO 87/07898 A1 | 12/1987 |
| WO | 92/20349 | 11/1992 |
| WO | WO 99/01166 | 1/1999 |

OTHER PUBLICATIONS

H. Hakert et al.: "Rheological and electron microscopic characterization of aqueous carboxymethyl cellulose gels Part I: Rheological aging of aqueous gels of carboxylmethyl cellulose in the free acid form (HCMC)" Colloid & Polym. Sci., vol. 267, pp. 226-229 1989.

(Continued)

Primary Examiner—Johann R. Richter
Assistant Examiner—Ernst V Arnold
(74) Attorney, Agent, or Firm—Oblon, Spivak, McClelland, Maier & Neustadt, P.C.

(57) ABSTRACT

(1) A tissue-covering medical material which comprises a soluble cellulose derivative having been made hardly soluble in water, which is used with a purpose of being embedded in the body or applied to the tissue, and (2) a method for producing the tissue-covering medical material as defined in (1), which comprises, as a method to make a soluble cellulose derivative hardly soluble in water, freezing and thawing an acidic solution of the soluble cellulose derivative, are provided.

14 Claims, 1 Drawing Sheet

OTHER PUBLICATIONS

T. Mueller et al.: "Rheological and electron microscopic characterization of aqueous carboxymethyl cellulose gels Part II: Visualization of the gel structure by freeze-fracturing" Colloid & Polym. Sci., vol. 267, pp. 230-236 1989.

Charlotte K. Ryan et al.: "Evaluation of a carboxymethylcellulose sponge for prevention of postoperative adhesions" The American Journal of Surgery, vol. 169, pp. 154-160 Jan. 1995.

S. Rossi et al.: "Drug release and washability of mucoadhesive gels based on sodium carboxymethylcellulose and polyacrylic acid" Pharmaceutical Development and Technology, vol. 4, No. 1, pp. 55-63 1999.

Dang Duc Long et al.: "Chitosan-carboxymethylcellulose hydrogels as supports for cell immobilization" J.M.S.—Pure Appl. Chem., vol. A33, No. 12, pp. 1875-1884 1996.

"Sodium carboxymethylcellulose" Encyclopedia of Polymer Science and Technology, vol. 3, pp. 520-539 1965.

Jerry March, " Advanced Organic Chemistry Reactions, Mechanisms, and Structure", Aliphatic Nucleophilic Substitution, Fourth Edition, pp. 393-396, 1992.

R. L. Feller, et al., "Evaluation of Clellulose Ethers for Conservation", Research in Conservation, 1990.

Ott, E. et al., "High Polymers", A Series of Monographs on the Chemistry, Physics and Technology of High Polymeric Substances, vol. V, 1943, pp. 784-787.

Thomas J. Heinz, et al., "Cellulose Derivatives, Modification, Characterization, and Nonstructures", ACS Symposium Series, Aug. 25-29, 1996, pp. 61-73, 162-173.

Klaus Niemelä, et al., "Identification of the Products of Hydrolysis of Carboxy-Methylcellulose", Carbohydrate Research, 180, 1998, pp. 43-52.

K. Dusek, et al., "Structure and Elasticity of Non-Crystalline Polymer Networks", Adv. Polymer Sci., vol. 6, 1969, pp. 1-21.

\* cited by examiner

USE OF SOLUBLE CELLULOSE DERIVATIVE HAVING BEEN MADE HARDLY SOLUBLE IN WATER AND PROCESS FOR PRODUCING THE SAME

TECHNICAL FIELD

The present invention relates to (1) a tissue-covering medical material formed by a soluble cellulose derivative having been made hardly soluble in water obtained by an acid treatment of a soluble cellulose derivative without using any chemical cross-linking agent or another chemical modifying agent, which is used as an adhesion preventive material or a wound dressing, with a purpose of aiding and accelerating tissue curing, and (2) a production method to provide a tissue-covering medical material obtained by freezing and thawing an acidic aqueous solution of a soluble cellulose derivative.

BACKGROUND ART

As a soluble cellulose derivative, methyl cellulose, hydroxyethyl cellulose, carboxymethyl cellulose, carboxymethylethyl cellulose and the like are known. Among them, carboxymethyl cellulose having a carboxymethyl group introduced thereinto (hereinafter, carboxymethyl cellulose means sodium carboxymethyl cellulose in accordance with general appellation) is a representative one, and is widely used in a food field or as e.g. a water-absorptive material utilizing its viscoelasticity, and its application extends to a medical field.

With respect to application of carboxymethyl cellulose to a medical field, a report has been made such that an effect of a carboxymethyl cellulose aqueous solution or one obtained by drying and molding it, as an adhesion preventive, has been confirmed, however, no adequate effect has been obtained (American Journal of Surgery, Vol. 169, 154-159 (1995)). JP-A-1-301624 and U.S. Pat. No. 5,906,997 disclose an adhesion preventive comprising a carboxymethyl cellulose composition using a chemical cross-linking agent or a chemical modifying agent, and an adhesion preventive in a film-form, which is a composition obtained by modifying hyaluronic acid and carboxymethyl cellulose with a carbodiimide, developed based on JP-A-5-508161 and JP-A-6-508169, "Sepra-film" (manufactured by Genzyme Corporation) is commercially available.

However, no example has been found wherein a carboxymethyl cellulose having been made hardly soluble in water, which is substantially unmodified, is used for an adhesion preventive.

With respect to a wound dressing, JP-A-11-322615 discloses a wound-curing agent comprising carboxymethyl cellulose and fibrin, JP-A-7-109220 discloses a wound-curing agent comprising carboxymethyl cellulose and a disinfectant, and German Patent No. 1397893 discloses a wound-curing agent comprising carboxymethyl cellulose and an anti-inflammatory agent. Further, JP-A-8-505258 and European Patent No. 47647 disclose a wound dressing comprising a crosslinked carboxymethyl cellulose. All of them comprise a soluble carboxymethyl cellulose or carboxymethyl cellulose crosslinked by means of e.g. a chemical cross-linking agent, and a use of carboxymethyl cellulose having been made hardly soluble in water, which is unmodified, as a wound dressing, is not disclosed similar to the case of an adhesion preventive.

On the other hand, as an implant in a form of a block to be used with a purpose of bone repair, for example, JP-A-62-39506 discloses a porous sponge having chitin crosslinked therewith by means of a chemical, JP-A-3-23864 discloses a composite material in a form of a block comprising a collagen sponge and polylactic acid, and JP-A-7-505643 discloses an excellent bone-substituting agent having biocompatibility and bioabsorptivity, comprising a hyaluronate. However, a porous sponge is non-absorptive in the body, whereby it is not completely substituted by the bone, and there are a risk of infection and a risk of the material itself being separated, and further, in a case where collagen is used, there is such a defect that atelocollagen has a slight antigenicity.

Further, a chemical carrier (Pharm. Develop. Tech., Vol. 4, 55-63 (1999)), a cell culture medium (J. M. S.—Pure Appl. Chem., Vol. A33, 1875-1884 (1996)), a polypeptide growth factor-containing gel composition (U.S. Pat. No. 5,705,485) and the like are reported or disclosed, but in all cases, carboxymethyl cellulose to be used is different from that in the present invention.

Conventionally, for example, to improve material characteristics such as viscoelasticity of carboxymethyl cellulose for example, a chemically crosslinked carboxymethyl cellulose by means of glyoxal as disclosed in JP-A-10-251447, a carboxymethyl cellulose gel mixed with multivalent metal ions as disclosed in JP-A-63-37143, a carboxymethyl cellulose gel by means of a bivalent or trivalent metal salt as disclosed in JP-A-7-090121, and a carboxymethyl cellulose gel by addition of a basic aluminum acetate as disclosed in JP-A-11-106561, has been considered. However, to such a modified carboxymethyl cellulose, a chemical cross-linking agent is used or metal ions are added, and a material containing no such material has been desired in view of safety when used as medical products.

As the method to obtain a carboxymethyl cellulose having been made hardly soluble in water, a method of leaving an acidic solution of carboxymethyl cellulose to stand (Encyclopedia of Polymer Science & Technology, Vol. 3, 520-539 (1965)), a method of adding a strong acid to a granular carboxymethyl cellulose in the presence of methyl alcohol or ethyl alcohol (Colloid Polym. Sci., Vol. 267, 226-236 (1989)) and a method of using a strong ionic cation exchange resin (U.S. Pat. No. 2,617,800) may, for example, be mentioned. Further, a method of concentrating an acidic solution of carboxymethyl cellulose by means of ultracentrifugation may also be used. However, in these methods, there are problems in handling properties and time until a carboxymethyl cellulose having been made hardly soluble in water is obtained, yield, and such a problem that it tends to be difficult to form the obtained carboxymethyl cellulose having been made hardly soluble in water into a sheet, film, sponge or tube.

In order to achieve the above objects, the present inventors have conducted extensive studies on physicochemical characteristics of the soluble cellulose derivative itself and its effect on the body. As a result, they have found that a soluble cellulose derivative having been made hardly soluble in water, obtained by an acid treatment, which has conventionally been reported, has a high effect as a tissue-covering medical material such as an adhesion preventive or a wound dressing. Further, they have found that a material produced by a means of freezing and thawing a soluble cellulose derivative aqueous solution under an acidic condition, which has not conventionally been studied, has a fibrous or fill-like fine structure due to an effect of ice crystals formed during freezing. It was clarified that the soluble cellulose derivative having been made hardly soluble in water obtained by freezing and thawing is not only easily formed into a sheet, a film, a sponge or the like, but also easily formed into a sheet, a film, a tube or the like in a uniform form after it is crushed by means of a mixer or supersonic wave, and it has excellent material characteristics as a medical material, as compared with a soluble cellulose derivative having been made hardly soluble in water prepared by an acid treatment which has conventionally been known.

Further, with respect to adaptability in application to the body, candidates which have a controlled solubility which is an important physical property, and which has an extremely high adhesion preventive effect and high adaptability could be found, and the present invention has been accomplished.

DISCLOSURE OF THE INVENTION

Namely, the present invention provides (1) a tissue-covering medical material which comprises a soluble cellulose derivative having been made hardly soluble in water, which is used with a purpose of being embedded in the body or applied to the tissue, (2) a method for producing the tissue-covering medical material as defined in (1), which comprises, as a method to make a soluble cellulose derivative hardly soluble in water, freezing and thawing an acidic solution of the soluble cellulose derivative, (3) the tissue-covering medical material according to (1), wherein a soluble cellulose derivative having been made hardly soluble in water obtained by mixing a soluble cellulose derivative with an acid solution so that the concentration of the soluble cellulose derivative is at least 5 mass %, and leaving the admixture to stand at a non-freezing temperature, is used, (4) the tissue-covering medical material according to (1), wherein a soluble cellulose derivative having been made hardly soluble in water obtained by leaving an acidic solution of a soluble cellulose derivative to stand, is used, (5) the tissue-covering medical material according to (1), wherein a soluble cellulose derivative having been made hardly soluble in water obtained by mixing an acidic solution of a soluble cellulose derivative with a polar organic solvent, is used, (6) the tissue-covering medical material according to (1), wherein a soluble cellulose derivative having been made hardly soluble in water obtained by passing a soluble cellulose derivative solution through a cation exchange column, is used, (7) the tissue-covering medical material according to (1), wherein a soluble cellulose derivative having been made hardly soluble in water obtained by concentrating an acidic solution of a soluble cellulose derivative, is used, (8) the soluble cellulose derivative having been made hardly soluble in water according to (1), which comprises a soluble cellulose derivative, and which is substantially unmodified by a chemical cross-linking agent, a chemical modifying agent or the like, (9) the tissue-covering medical material according to (1) or (2), wherein the soluble cellulose derivative having been made hardly soluble in water has a fibrous structure or a film-form structure, (10) the tissue-covering medical material according to (1), wherein the percentage dissolution of the soluble cellulose derivative is at most 50% in 3 hours in a neutral aqueous solution of 60° C., (11) the method for producing the tissue-covering medical material according to (2), wherein the solubility of the soluble cellulose derivative having been made hardly soluble in water is controlled, (12) the tissue-covering medical material according to (1), which comprises the soluble cellulose derivative having been made hardly soluble in water and a high polymer other than hyaluronic acid or a hyaluronate, (13) the soluble cellulose derivative according to any one of (1) to (12), wherein the soluble cellulose derivative is carboxymethyl cellulose, (14) the tissue-covering medical material according to (1) or (12), wherein the tissue-covering medical material is an adhesion preventive, (15) the tissue-covering medical material according to (1) or (12), wherein the tissue-covering medical material is a wound dressing, and (16) the tissue-covering medical material according to (1) or (12), wherein the tissue-covering medical material is a covering material for bone repair.

BEST MODE FOR CARRYING OUT THE INVENTION

Now, the present invention will be explained in detail below.

To be imbedded in the body or applied to the tissue in the present invention means to be applied to a tissue such as mucous membrane in the body, blood vessel, bone or cord or an organ such as stomach or intestine, or skin or mucous membrane on the body surface. For example, it means to apply the medical material to a surgical damage caused in a common surgery, a physical damage such as bone fracture, rupture of Achilles tendon or decubitus, or a chemical damage such as burn injury by a chemical. Further, the tissue-covering medical material means a biocompatible material to be used for covering a tissue or an organ which is damaged or impaired regardless of in the body or outside the body.

In the present invention, as the soluble cellulose derivative, methyl cellulose, ethyl cellulose, hydroxyethyl cellulose, hydroxypropyl cellulose, carboxymethyl cellulose, carboxymethylethyl cellulose or the like may be used, and most preferred is carboxymethyl cellulose which is easily available at an industrial level at a low cost.

The molecular weight of the soluble cellulose derivative to be used in the present invention is not particularly limited, but preferably within a range of from about $1 \times 10^4$ to about $5 \times 10^5$ Da.

Further, so long as it is one having a molecular weight within the above range, even one obtained from one having a higher molecular weight by e.g. hydrolytic treatment may likewise preferably be used. Further, with respect to the etherification degree which is the other parameter of the soluble cellulose derivative, one within a range at which it can be made hardly soluble in water by the following treatment can be used.

Here, the soluble cellulose derivative of the present invention is used in a concept which includes also its alkali metal salt such as a sodium, potassium or lithium salt.

The modification in the present invention means to introduce a chemical cross-linking or to carry out chemical modification to make a soluble cellulose derivative which is naturally soluble in water to be hardly soluble in water.

To control the solubility in the present invention means to change the ratio of the soluble cellulose derivative which elutes into a phosphate-buffered physiological saline after a certain time, when the soluble cellulose derivative having been made hardly soluble in water is left in a phosphate-buffered physiological saline of pH 7.4 at 60° C., as explained in the following examples.

Production of the soluble cellulose derivative by the freezing and thawing method will be described below. As an acid to be used to adjust the pH of the aqueous solution of the soluble cellulose derivative, any acid may be used so along as it is an acid capable of adjusting the pH to be at most 3.5. In order to reduce the amount of the acid, it is preferred to use a strong acid such as hydrochloric acid, nitric acid or sulfuric acid. Here, the pH of the acidic aqueous solution is selected depending upon e.g. the molecular weight and the etherification degree of the soluble cellulose derivative to be used, and physical properties of an aimed soluble cellulose derivative having been made hardly soluble in water, and more preferred is pH 2 or lower.

For freezing and thawing, an operation is carried out at least once wherein an acidic aqueous solution having the soluble cellulose derivative adjusted is put into an optional container and then frozen at a predetermined temperature, and after completion of the freezing, thawing is carried out at a predetermined temperature. The temperatures and times for freezing and thawing may suitably be determined within ranges of the temperatures and the times for freezing and thawing of the acidic aqueous solution of the soluble cellulose derivative, depending upon the size of the container and the amount of the aqueous solution. However, usually, preferred are a freezing temperature of at most freezing point and a thawing temperature of at least freezing point.

Since the freezing and thawing times can be shortened, a freezing temperature of at most −5° C. and a thawing temperature of at least 5° C. are selected more preferably. Further, the times are not particularly limited so long as they are sufficient to complete the freezing and thawing at the respective temperatures.

The number of repetitions of the operation of freezing the acidic aqueous solution having the soluble cellulose derivative adjusted, followed by thawing, is suitably determined depending upon the molecular weight of the soluble cellulose derivative to be used, the aqueous solution concentration, the pH of the aqueous solution, the temperatures and times of the freezing and thawing, and various properties such as strength of the soluble cellulose derivative having been made hardly soluble in water to be formed. Usually, it is preferred to repeat the operation at least once. Further, the temperatures and times for the freezing and thawing may be changed every time when the operation of freezing and thawing is repeated.

The solubility of the soluble cellulose derivative having been made hardly soluble in water to be obtained can easily be controlled by suitably selecting the molecular weight of the soluble cellulose derivative to be used, the pH of the aqueous solution, the temperature and time for freezing and the like. For example, in a case where sodium carboxymethyl cellulose having a calculated molecular weight of from $1.28 \times 10^5$ to $1.35 \times 10^5$ Da is dissolved in distilled water so that it becomes 1 mass %, pH of the aqueous solution is adjusted to 1.5, and this aqueous solution is frozen at −20° C. and thawed at room temperature, the longer the freezing time, the less soluble the carboxymethyl cellulose having been hardly soluble in water to be obtained will be.

Further, in a case where an aqueous solution of pH 1.5 of sodium carboxymethyl cellulose having a different molecular weight, prepared to have the same concentration, is frozen at −20° C. for a predetermined time and then thawed at room temperature, the higher the molecular weight of the sodium carboxymethyl cellulose, the less soluble the carboxymethyl cellulose having been made hardly soluble in water to be obtained will be.

Further, when the pH alone of the sodium carboxymethyl cellulose aqueous solution is changed to compare a case of pH 1.5 with a case of pH 2, a carboxymethyl cellulose having been made hardly soluble in water having a lower pH is less likely to be soluble.

Now, a method of mixing the soluble cellulose derivative with an acid solution at a concentration of at least 5 mass % will be described below. As the acid to be mixed, any acid may be used. In order to reduce the amount of the acid, it is preferred to use a strong acid such as hydrochloric acid, nitric acid or sulfuric acid. For mixing and leaving to stand, an operation is carried out at least once wherein the soluble cellulose derivative and the acidic solution are put into an optional container, followed by thorough mixing until the mixture becomes uniform, and after completion of the mixing, the mixture is left to stand at a predetermined temperature. The temperatures and times for mixing and leaving to stand are suitably determined depending upon the size and capacity of the container, however, usually preferred is the mixing temperature of at most room temperature. Further, the time for leaving to stand is not particularly limited so long as it is sufficient to complete the above operation.

Then, the method for producing the soluble cellulose derivative having been made hardly soluble in water by another production method will be described below. As a conventionally known method of leaving a soluble cellulose derivative acidic solution to stand, any method may be employed so long as an acidic aqueous solution of a soluble cellulose derivative can be obtained, such as a method of dissolving a soluble cellulose derivative in water and adding e.g. hydrochloric acid, nitric acid or sulfuric acid to the resulting aqueous solution for acidification or a method of dissolving a soluble cellulose derivative in an acidic solution.

The concentration of the soluble cellulose derivative in the acidic solution is not particularly limited, but it is preferably at most 5 mass %, more preferably at most 1 mass %, since the solution may have viscosity. The pH of the acidic aqueous solution is selected depending upon e.g. the molecular weight and the etherification degree of the soluble cellulose derivative and physical properties of an aimed soluble cellulose derivative having been made hardly soluble in water. However, preferably pH is at most 3.5, more preferably pH is at most 2.

By leaving the prepared acidic solution of the soluble cellulose derivative to stand, a soluble cellulose derivative having been made hardly soluble in water can be obtained, and the time for leaving to stand is selected depending upon e.g. the molecular weight and the etherification degree of the soluble cellulose derivative to be used and physical properties of an aimed soluble cellulose derivative having been made hardly soluble in water, similar to the pH of the acidic solution.

Further, the temperature for leaving to stand is not particularly limited so long as the above operation is completed at the temperature, but is usually preferably at most room temperature, more preferably a temperature of at most 5° C. and at which the soluble cellulose derivative acidic aqueous solution is not frozen.

The soluble cellulose derivative having been made hardly soluble in water can also be obtained by mixing an acidic aqueous solution of a soluble cellulose derivative with a polar organic solvent such as methanol or ethanol. The concentration of the soluble cellulose derivative in the acidic solution is not particularly limited, but is preferably at most 5 mass %, more preferably at most 1 mass %. Further, the pH is selected depending upon e.g. the molecular weight and the etherification degree of the soluble cellulose derivative to be used and physical properties of an aimed soluble cellulose derivative having been made hardly soluble in water. However, preferably pH is at most 3.5, more preferably pH is at most 2.

The polar organic solvent means a water-soluble organic compound which is completely compatible with water and which has a polarity so that the soluble cellulose derivative is dissolved in a mixed solvent of the polar organic solvent with water at room temperature or at a temperature of at least room temperature to form a solution.

The polar organic solvent to be used in the present invention is not particularly limited so long as the soluble cellulose derivative having been made hardly soluble in water can be obtained, and a lower alcohol type solvent such as methanol or ethanol, a polyhydric alcohol type solvent such as glycerol or ethylene glycol, a ketone type solvent such as acetone or methyl ethyl ketone, an ether type solvent such as dioxane or tetrahydrofuran, an amide type solvent such as formamide or N,N-dimethylformamide, a sulfoxide type solvent such as dimethylsulfoxide or tetrahydrothiophene-1, a phosphoric amide type solvent such as hexamethylphosphoric triamide, or acetonitrile may, for example, be used. Said polar organic solvent may be used alone or in combination as a mixture of at least two.

Such a polar organic solvent may be added all at once, or it may further be added to the acidic solution after the soluble cellulose derivative having been made hardly soluble in water is recovered, and the addition method is by no means restricted. Further, an acidic aqueous solution of the soluble cellulose derivative may be prepared and the polar organic solvent may be added in an appropriate amount to said aqueous solution, or a powder of the soluble cellulose derivative may be directly dissolved in a mixed solvent of the polar organic solvent with water and then the solution may be acidified.

In a method of passing the soluble cellulose derivative aqueous solution through a cation exchange column, a column packed with a strongly ionic cation exchange resin may, for example, be used. The concentration of the soluble cellulose derivative is selected depending upon e.g. the molecular weight and the etherification degree of the soluble cellulose derivative. However, it is preferably at most 1 mass %, more preferably at most 0.5 mass %.

The ion exchange resin to be used is not particularly limited so long as it has a performance to exchange sodium in the soluble cellulose derivative for hydrogen, and preferred is a strongly ionic cation exchange resin having a sulfone group.

In a case where the acidic aqueous solution of the soluble cellulose derivative is concentrated, as a concentration method, ultracentrifugation, drying by ventilation, vacuum drying or freeze drying may, for example, be mentioned. The concentration of the soluble cellulose derivative in the acidic aqueous solution before concentration is usually preferably at most 5 mass %, more preferably at most 1 mass %, in view of handling efficiency.

Now, moldability of the soluble cellulose derivative having been made hardly soluble in water in a case of application as a medical material will be described below. First, it is required to carry out an operation of removing and washing off the used acid for adaptation to the body. Removal of the acid is carried out by replacement of the liquid around the soluble cellulose derivative having been made hardly soluble in water by means of a neutral buffer, and in a case where inclusion of the buffer component is inconvenience, replacement by purified water is carried out to obtain a soluble cellulose derivative having been made hardly soluble in water. The neutral buffer to be used is not particularly limited so long as it does not impair a function of the soluble cellulose derivative having been made hardly soluble in water, and a pharmacologically acceptable phosphate buffer may, for example, be used.

Further, the neutralization method is not particularly limited, and usually a batch method, a filtration method or a method of passing the liquid through a packed column may, for example, be used. The neutralization conditions including the amount of the neutralization liquid and frequency, may be conditions under which a component such as an acid used to adjust the liquid to be acidic can be neutralized, and may be optionally selected depending upon the form or application of the soluble cellulose derivative having been made hardly soluble in water.

The soluble cellulose derivative having been made hardly soluble in water thus obtained may be used in a state where it is immersed in a solvent, in a wet state where a solvent is contained, or a dry state where it is subjected to a treatment such as drying by ventilation, vacuum drying or freeze drying, depending upon the specific purpose of use.

With respect to treatment such as molding of the soluble cellulose derivative having been made hardly soluble in water, at the time of preparation, by selection of a method or a container for the soluble cellulose derivative and the prepared soluble cellulose derivative acidic aqueous solution, it is possible to prepare a soluble cellulose derivative having been made hardly soluble in water in a desired form such as a sheet-form, a film-form, a crushed form, a sponge-form, a bulk form, a fiber-form or a tube-form. As molding after preparation of the soluble cellulose derivative having been made hardly soluble in water, micro crushing by mechanical grinding, film forming by rolling, fiber forming or the like may be carried out.

With respect to the freezing and thawing method, a soluble cellulose derivative having been made hardly soluble in water in a form of a square or round sheet, film, sponge or the like, can be obtained by using, for example, a square or round container at the time of freezing. Further, a once obtained soluble cellulose derivative having been made hardly soluble in water may be crushed by means of e.g. a mixer in distilled water or physiological saline to obtain a suspension of the soluble cellulose derivative having been made hardly soluble in water, or the suspension may be dried in a container to form the derivative into a sheet-form, a film-form, a bulk form or the like. Further, the soluble cellulose derivative having been made hardly soluble in water obtained by the freezing and thawing method has a fiber-form or film-form structure, and accordingly it is easy to form the derivative into a uniform sheet-form or film-form by expanding the suspension on e.g. a filter having pores which are sufficient to capture the soluble cellulose derivative having been made hardly soluble in water, followed by drying.

Further, a high molecular compound may be mixed with the soluble cellulose derivative having been made hardly soluble in water of the present invention. The high molecular compound is not particularly limited so long as it has no adverse effect such as inflammatory effect or impairing effect on the tissue, and any of a natural high molecular compound, a synthetic high molecular compound, a water-soluble high molecular compound and a water-insoluble high molecular compound may be used. Such a compound may be mixed with the acidic solution of the soluble cellulose derivative at the time of preparation of the soluble cellulose derivative having been made hardly soluble in water, or may be mixed with the prepared soluble cellulose derivative having been made hardly soluble in water, and the method is not particularly limited so long as it does not prevent the soluble cellulose derivative from being made hardly soluble in water.

Typical examples of the high molecular compound to be mixed, are selected from the group consisting of polysaccharides, proteins, nucleic acids and synthetic high polymers, but is not limited thereto.

Examples of polysaccharides include glycosaminoglycans except for hyaluronic acid or a hyaluronate (such as heparin, heparan sulfate and dermatan sulfate), chondroitin sulfates (such as chondroitin-6-sulfate), keratin sulfates, alginic acid its biologically acceptable salts, cellulose, chitin, chitosan, dextran, starch, amylose, polylactic acid and karaginan.

Further, examples of proteins include collagen, gelatin, albumin, elastin, various globulins, casein, gluten and their biologically acceptable synthetic derivatives.

Further, examples of synthetic high polymers include polyvinyl alcohol, polyethylene glycol, polyglycolic acid, polyacrylic acid, polymethacrylic acid, polylactic acid, their copolymers, and derivatives such as poly(hydroxyethyl)acrylates or methacrylates, polyacrylamides, polyvinyl alcohols, and copolymers of maleic acid or fumaric acid.

Here, the present invention is by no means restricted to such high polymer compounds.

Now, sterilization treatment required for a medical device will be described below. The sugar chain structure of the soluble cellulose derivative is relatively stable against e.g. heat or radiation, and accordingly various sterilization methods such as γ-ray sterilization, electron ray sterilization, sterilization by ethylene oxide gas or sterilization by plasma gas can be applied to a tissue-covering medical material comprising a soluble cellulose derivative having been made hardly soluble in water. A phenomenon is confirmed such that the solubility of the soluble cellulose derivative having been made hardly soluble in water changes by such a severe treatment, however, it is possible to preliminarily produce a more stable material by changing production conditions such as a freezing time in the freezing and thawing method so as to control retention property in the body.

Now, an adhesion preventive among the medical materials of the present invention will be explained below.

The adhesion preventive comprising the soluble cellulose derivative having been made hardly soluble in water obtained according to the present invention can be used for a surgery in a form of e.g. a sheet, a film, a crushed product, a sponge, an agglomerate, fibers, a fluid or a tube. With respect to the mode of use, it is preferred to apply a film-form or sheet-form material directly to a part subjected to surgery. It is also preferred to apply a fine crushed product or a fluid by injection to a part subjected to surgery. It can also be used for peritoneoscopical surgery.

Now, a wound dressing among the medical materials of the present invention will be explained below.

The wound dressing comprising the soluble cellulose derivative having been made hardly soluble in water obtained according to the present invention can be used in a form of e.g. a sheet, a film, a crushed product, a sponge, an agglomerate, fibers, a fluid or a tube. With respect to the mode of use, it is preferred to apply a film-form or sheet-form material directly to an affected portion, and it can optionally be selected depending upon the shape or the size of the wound.

Now, the present invention will be explained in further detail with reference to Examples. However, the present invention is by no means restricted thereto.

EXAMPLE 1

Sodium carboxymethyl cellulose having a 1% viscosity of from 150 to 250 mPa·s at 25° C. (etherification degree: 0.62-0.68, calculated molecular weight: $1.28 \times 10^5 - 1.35 \times 10^5$ Da, manufactured by Dai-ichi Kogyo Seiyaku Co., Ltd.) was dissolved in distilled water so that it became 1 mass %. The pH of the aqueous solution thus prepared was adjusted to 1.5 with 1N nitric acid, and 15 ml of the acidic aqueous solution was put in a polystyrene container of 30 ml and placed in a freezer set at −20° C. It was left to stand for three days and then thawed at 25° C. Then, neutralization was carried out with water and a phosphate buffer having a concentration of 100 mM (pH 6.8) to obtain a spongy carboxymethyl cellulose having been made hardly soluble in water. This carboxymethyl cellulose having been made hardly soluble in water was freeze-dried to obtain a sheet containing about 1.5 mg/cm$^2$.

EXAMPLE 2

The carboxymethyl cellulose used in Example 1 was admixed with 1N nitric acid at room temperature so that it became 20 mass %, and the admixture was preserved in a refrigerator of 4° C. for three days. Then, neutralization was carried out with water and a phosphate buffer having a concentration of 100 mM (pH 6.8) to obtain an agglomerated carboxymethyl cellulose having been made hardly soluble in water. This carboxymethyl cellulose having been made hardly soluble in water was rolled by applying a pressure of about 30 N/cm$^2$ thereto, followed by drying at about 50° C. to obtain a film containing about 1.5 mg/cm$^2$.

EXAMPLE 3

The carboxymethyl cellulose used in Example 1 was dissolved in distilled water so that it became 1 mass %. The pH of the aqueous solution thus prepared was adjusted to 1.0 with 1N nitric acid, and 3 l of the acidic aqueous solution was put in a container of 4 l and preserved in a refrigerator of 4° C. for 40 days. Deposited carboxymethyl cellulose having been made hardly soluble in water was recovered by centrifugal separation, and neutralization was carried out with water and a phosphate buffer having a concentration of 100 mM (pH 6.8) to obtain an agglomerated carboxymethyl cellulose having been made hardly soluble in water. This carboxymethyl cellulose having been made hardly soluble in water was suspended in physiological saline, followed by casting into a polystyrene container and drying at about 50° C. to obtain a film containing about 1.5 mg/cm$^2$.

EXAMPLE 4

The carboxymethyl cellulose used in Example 1 was dissolved in distilled water so that it became 1 mass %. The pH of the aqueous solution was adjusted to 1.0 with 1N nitric acid, and dimethylsulfoxide was added thereto so that it became 5 mass %. 100 ml of this solution was put in a glass bottle of 200 ml and preserved in a freezer of 4° C. for 10 days to obtain finely granular carboxymethyl cellulose having been made hardly solved in water. Neutralization was carried out with water and a phosphate buffer having a concentration of 100 mM (pH 6.8), and then the carboxymethyl cellulose having been made hardly soluble in water was suspended in physiological saline, followed by casting into a polystyrene container and drying at about 50° C. to obtain a film containing about 1.5 mg/cm$^2$.

EXAMPLE 5

The carboxymethyl cellulose used in Example 1 was dissolved in distilled water so that it became 0.3 mass %. The solution was packed in a glass column having an inner diameter of about 5 cm and a length of about 15 cm packed with TSKgel SP-TOYOPEARL550, followed by equilibration by means of a 0.5 mmol/l phosphoric acid. The prepared carboxymethyl cellulose solution was injected into an ion exchange column by means of a pump for liquid chromatography P-500, and a 0.5 mmol/l phosphoric acid was passed therethrough at a flow rate of 0.5 ml/min to obtain a viscous solution of a carboxymethyl cellulose having been made hardly soluble in water. Adequate dialysis was carried out against water and a phosphate buffer having a concentration of 100 mM (pH 6.8) and the obtained solution of the carboxymethyl cellulose having been made hardly soluble in water was put in a polystyrene container and freeze-dried to obtain a sheet containing about 1.2 mg/cm$^2$.

EXAMPLE 6

The carboxymethyl cellulose used in Example 1 was dissolved in distilled water so that it became 2 mass %. The pH of this aqueous solution was adjusted to 1.5 with 1N nitric acid, and 15 ml of the acidic aqueous solution was put in a container of 30 ml and dried by vacuum drying set at 80° C. to obtain a carboxymethyl cellulose having been made hardly soluble in water in a form of a film. This carboxymethyl cellulose having been made hardly soluble in water was neutralized with water and a phosphate buffer having a concentration of 100 mM (pH 6.8) and then dried at about 50° C. again to obtain a film containing about 1.8 mg/cm$^2$.

EXAMPLE 7

Adhesion Preventive Test on a Rat Appendix Abraded Model Adhesion Inducing Method A rat (SD, female, at least 9 weeks old) was anesthetized by intramuscular injection of an anesthetic (ketamine solution) and fixed on its back. After disinfecting the abdominal skin with isodine, shaving hair was carried out. The abdominal muscle of the rat was cut along the midline. The appendix was taken out from the abdominal cavity, and the appendix was fixed by means of a porous (Φ16 mm) Tefron sheet. The appendix portion exposed through pores was abraded by pressing a rotating rod (Φ13 mm) covered with a gauge about 120 times (2 portions on each side). A piece of about 4 cm×4 cm of each of the carboxymethyl celluloses having been made hardly soluble in water obtained in Examples 1 to 6 was placed at the abraded portion, and the appendix was returned to the initial position, followed by suturing. One having the appendix returned to the initial position without applying the adhesion preventive was used as control. For seven to ten rats were used for each test including the control. About one week after the operation, ventrotomy was performed, and scoring was carried out based on the following evaluation standards (Fertility and Sterility 66, 5, 814-821) to evaluate the adhesion preventive effect. The results are shown in Table 1.
Evaluation standards
0: No adhesion
1: Film-form adhesion having a face which can readily be confirmed
2: A slight adhesion having a face which can freely be peeled off
3: A medium adhesion, the face of which can hardly be peeled off
4: A dense adhesion having a face which cannot be peeled off

TABLE 1

| Test No. | Adhesion score | Incidence of adhesion (%) | Note |
| --- | --- | --- | --- |
| 1 | 0.6 | 35 | Ex. 1 |
| 2 | 0.7 | 46 | Ex. 2 |
| 3 | 1.2 | 55 | Ex. 3 |
| 4 | 1.1 | 61 | Ex. 4 |
| 5 | 0.9 | 32 | Ex. 5 |

TABLE 1-continued

| Test No. | Adhesion score | Incidence of adhesion (%) | Note |
| --- | --- | --- | --- |
| 6 | 1.3 | 49 | Ex. 6 |
| 7 | 1.7 | 85 | Control |

As evident from Table 1, the adhesion score was 1.7 in control, whereas the scores of the sheets and films obtained in Examples 1 to 6 were from 0.6 to 1.3, and an adhesion preventive effect by the carboxymethyl cellulose having been made hardly soluble in water was found.

EXAMPLE 8

Figure 1:
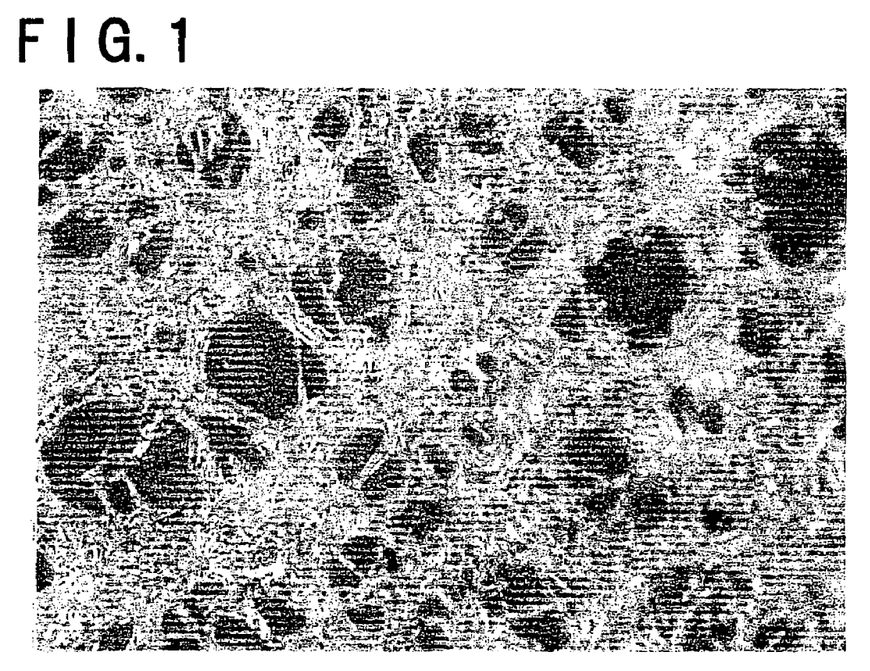
FIG. 1 illustrates a carboxymethyl cellulose having been made hardly soluble in water, obtained by a freezing and thawing treatment.
Figure 2:
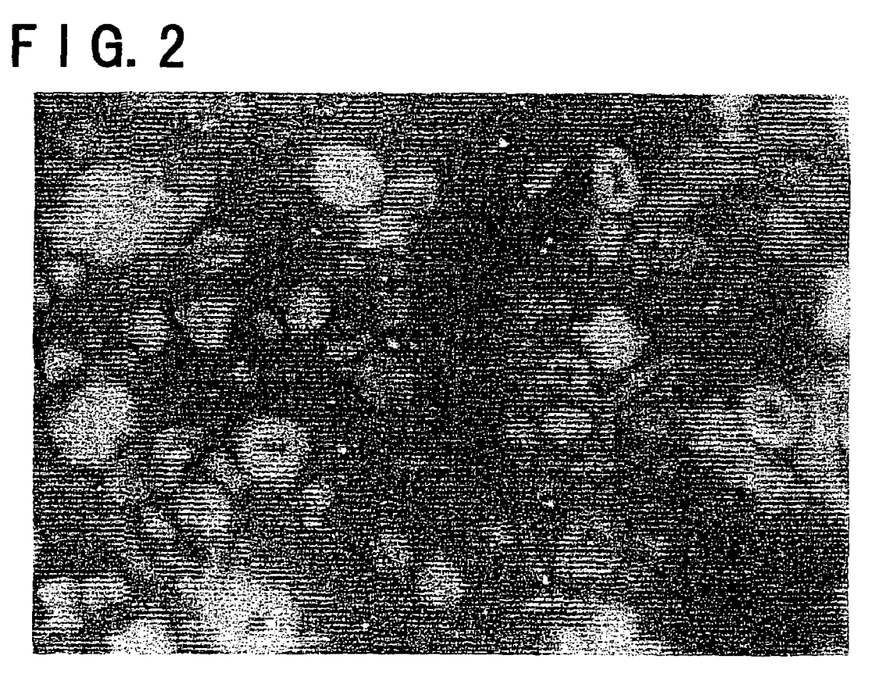
FIG. 2 illustrates a carboxymethyl cellulose having been made hardly soluble in water obtained by an acidic aqueous solution aging treatment.

Microscopic Observation of Carboxymethyl Cellulose having been made Hardly Soluble in Water Each of the carboxymethyl celluloses having been made hardly soluble in water obtained in Examples 1 to 4 was neutralized with water and a phosphate buffer having a concentration of 100 mM (pH 6.8) and then dried at about 50° C. Each of them was observed by using digital microscope (model VH-7000, manufactured by Keyenece Corporation). As a result, a fibrous structure or a film-form structure was observed only in the carboxymethyl cellulose having been made hardly soluble in water obtained in Example 1. Figures (photographs) of the carboxymethyl cellulose having been made hardly soluble in water obtained in Example 1 and the carboxymethyl cellulose having been made hardly soluble in water obtained in Example 3 as a comparison are shown.

The obtained carboxymethyl cellulose having been made hardly soluble in water was crushed in distilled water by means of a micro homogenizer (NISSEI EXCEL AUTO HOMOGENIZAER) to obtain a slurry, and the slurry was expanded on a screen for printing and dried to obtain a film. A uniform film was obtained with the carboxymethyl cellulose having been made hardly soluble in water obtained in Example 1 as shown in FIG. 1, whereas with another carboxymethyl cellulose having been made hardly soluble in water as shown in FIG. 2, the film was non-uniform.

EXAMPLE 9

The carboxymethyl cellulose used in Example 1 was dissolved in distilled water so that it became 1 mass %. The pH of the aqueous solution thus prepared was adjusted with 1N nitric acid to 1.5, and 15 ml of the acidic aqueous solution was put into a polystyrene container of 30 ml and placed in a freezer set at −20° C. It was left to stand for 5 days, and then thawed at 25° C. Then, neutralization was carried out with water and a phosphate buffer having a concentration of 100 mM (pH 6.8) to obtain a spongy carboxymethyl cellulose having been made hardly soluble in water.

EXAMPLE 10

Sodium carboxymethyl cellulose (etherification degree: 0.65 to 0.95, calculated molecular weight: about 3.0×10$^5$ Da, manufactured by Hercules Incorporated) having a 1% viscosity at 25° C. of from 1,000 to 2,800 mPa·s, was dissolved in distilled water so that it became 1 mass %. The pH of the aqueous solution thus prepared was adjusted with 1 N nitric acid to 1.5, and 15 ml of the acidic aqueous solution was put into a 30 ml container and placed in a freezer set at −20° C. It was left to stand for one day and then thawed at 25° C. Then, neutralization was carried out with water and a phosphate buffer having a concentration of 100 mM (pH 6.8) to obtain a spongy carboxymethyl cellulose having been made hardly soluble in water.

EXAMPLE 11

In Example 10, the time for leaving the solution to stand at −20° C. was three days, and a spongy carboxymethyl cellulose having been made hardly soluble in water was obtained.

COMPARATIVE EXAMPLE 1

In Example 1, without acidification, the aqueous solution of carboxymethyl cellulose was left to stand. As a result, no carboxymethyl cellulose having been made hardly soluble in water was obtained. This aqueous solution was freeze-dried to obtain a sponge.

COMPARATIVE EXAMPLE 2

In Example 10, without acidification, the aqueous solution of carboxymethyl cellulose was left to stand. As a result, no carboxymethyl cellulose having been made hardly soluble in water was obtained. This aqueous solution was freeze-dried to obtain a sponge.

EXAMPLE 12

Solubility Test of the Carboxymethyl Cellulose having been made Hardly Soluble in Water A phosphate-buffered physiological saline of pH 7.4 comprising the following composition was prepared.

| Phosphate-buffered physiological saline | |
|---|---|
| Potassium chloride | 0.02 mass % |
| Potassium phosphate monobasic | 0.02 mass % |
| Sodium phosphate dibasic 12-water | 0.29 mass % |
| Sodium chloride | 0.81 mass % |

Each of the obtained carboxymethyl celluloses having been made hardly soluble in water was immersed in the phosphate-buffered physiological saline in such a proportion that the carboxymethyl celluloses having been made hardly soluble in water containing 50 mg by dry weight of carboxymethyl cellulose was in 50 ml of the phosphate-buffered physiological saline. Further, the spongy carboxymethyl celluloses obtained in Examples 1 and 2 were immersed in the phosphate-buffered physiological saline in such a proportion that 50 mg each was in 50 ml of the phosphate-buffered physiological saline. The proportion of the carboxymethyl cellulose eluted into the phosphate-buffered physiological saline when being left to stand at 60° C. was obtained from the concentration of the carboxymethyl cellulose in the phosphate-buffered physiological saline.

Accordingly, the solubility of the carboxymethyl cellulose having been made hardly soluble in water in a neutral aqueous solution at 60° C. is one stipulated by the above test.

Measurement of the Carboxymethyl Cellulose Concentration

The concentration of the carboxymethyl cellulose in the phosphate-buffered physiological saline was obtained from a peak area as measured by a differential refractometer by using GPC. Namely, the phosphate-buffered physiological saline collected with time was filtrated by a filter of 0.45 μm and injected into GPC.

The results are shown in Table 2.

TABLE 2

| | Percentage dissolution of carboxymethyl cellulose (%) | | | |
|---|---|---|---|---|
| Test No. | 3 hours | 5 hours | 10 hours | Note |
| 8 | 24 | 35 | 55 | Ex. 1 |
| 9 | 20 | 32 | 60 | Ex. 2 |
| 10 | 27 | 40 | 63 | Ex. 3 |
| 11 | 33 | 48 | 70 | Ex. 4 |
| 12 | 39 | 51 | 69 | Ex. 5 |
| 13 | 25 | 39 | 59 | Ex. 6 |
| 14 | 18 | 24 | 47 | Ex. 9 |
| 15 | 25 | 35 | 53 | Ex. 10 |
| 16 | 2 | 8 | 14 | Ex. 11 |
| 17 | 95 | 100 | | Comp. Ex. 1 |
| 18 | 90 | 100 | | Comp. Ex. 2 |

For example, with respect to the carboxymethyl cellulose having been made hardly soluble in water obtained in Example 1 of Test No. 8, the percentage dissolution of the carboxymethyl cellulose was 24% after 3 hours, 35% after 5 hours and 55% after 10 hours. Namely, 76% after 3 hours, and 65% even after 5 hours, remained as the carboxymethyl cellulose having been made hardly soluble in water. With respect to the carboxymethyl celluloses having been made hardly soluble in water obtained in other Examples, similar results were obtained, and every carboxymethyl cellulose having been made hardly soluble in water had a percentage dissolution of the carboxymethyl cellulose after 3 hours of at most 50% in the solubility test.

On the contrary, in Comparative Examples 1 and 2 wherein no carboxymethyl cellulose having been made hardly soluble in water was obtained, the percentage dissolution of the carboxymethyl cellulose after 3 hours was at least 90%.

Further, from a comparison between Test No. 8 and Test No. 14, a comparison between Test No. 15 and Test No. 16, a comparison between Test No. 8 and Test No. 15, and a comparison between Test No. 14 and Test No. 16, it was clarified that the solubility can be controlled depending upon preparation conditions to be selected, with regard to the carboxymethyl cellulose having been made hardly soluble in water, obtained by freezing and thawing under acidic conditions.

EXAMPLE 13

In Example 10, the time for leaving the solution to stand at −20° C. was one day, and a spongy carboxymethyl cellulose having been made hardly soluble in water was obtained. This carboxymethyl cellulose having been made hardly soluble in water was freeze-dried to obtain a sheet containing about 2.0 mg/cm$^2$.

EXAMPLE 14

To the carboxymethyl cellulose having been made hardly soluble in water obtained in Example 13, γ-ray sterilization of 25 kGy produced from cobalt 60 as a radiation source was carried out.

EXAMPLE 15

In Example 10, the time for leaving the solution to stand at −20° C. was 7 days, and a spongy carboxymethyl cellulose having been made hardly soluble in water was obtained. This carboxymethyl cellulose having been made hardly soluble in water was freeze-dried to obtain a sheet containing about 2.0 mg/cm², and γ-ray sterilization of 25 kGy produced from cobalt 60 as a radiation source was carried out.

EXAMPLE 16

The carboxymethyl cellulose having been made hardly soluble in water obtained in Example 10 was freeze-dried to obtain a sheet containing about 2.0 mg/cm², and γ-ray sterilization of 25 kGy produced from cobalt 60 as a radiation source was carried out.

EXAMPLE 17

The carboxymethyl cellulose having been made hardly soluble in water obtained in Example 11 was freeze-dried to obtain a sheet containing about 2.0 mg/cm², and γ-ray sterilization of 25 kGy produced from cobalt 60 as a radiation source was carried out.

EXAMPLE 18

Solubility Test of the Carboxymethyl Cellulose having been made Hardly Soluble in Water Subjected to γ-Ray Sterilization In accordance with Example 12, solubility tests of the carboxymethyl celluloses having been made hardly soluble in water subjected to γ-ray sterilization, obtained in Examples 13 to 16, were carried out. The results are shown in Table 3.

TABLE 3

| Test No. | Percentage dissolution of carboxymethyl cellulose (%) | | | Note |
| --- | --- | --- | --- | --- |
| | 3 hours | 5 hours | 10 hours | |
| 19 | 20 | 33 | 61 | Ex. 13 |
| 20 | 80 | 95 | 100 | Ex. 14 |
| 21 | 7 | 11 | 21 | Ex. 15 |
| 22 | 44 | 58 | 70 | Ex. 16 |
| 23 | 25 | 42 | 63 | Ex. 17 |

From a comparison between Test No. 19 and Test No. 20, it was clarified that the solubility changes due to γ-ray sterilization. However, as shown in the results of Tests Nos. 20-23, it is also possible to control the solubility by preliminarily producing a more stable carboxymethyl cellulose having been made hardly soluble in water by changing the freezing time in the freezing and thawing method under acidic conditions.

EXAMPLE 19

Distilled water was added to the carboxymethyl cellulose having been made hardly soluble in water obtained in Example 11 so that the carboxymethyl cellulose concentration became 1 mass %, and crushing by means of a micro-homogenizer (NISSEI EXCEL AUTO HOMOGENIZAER) was carried out to obtain a slurry of the carboxymethyl cellulose having been made hardly soluble in water. This slurry was expanded on a screen for printing and dried at about 40° C. to obtain a film containing about 2.0 mg/cm² of the carboxymethyl cellulose having been made hardly soluble in water. Then, to the film, γ-ray sterilization of 25 kGy produced from cobalt 60 as a radiation source was carried out.

EXAMPLE 20

Adhesion Preventive Test of the Carboxymethyl Cellulose having been made Hardly Soluble in Water Obtained by the Freezing and Thawing Method In accordance with Example 7, an adhesion preventive test was carried out with respect to the sheet or film obtained in each of Examples 13, 16 and 19. Here, as a comparison, commercially available Seprafilm (manufactured by Genzyme Corporation) was used. The results are shown in Table 4.

TABLE 4

| Test No. | Adhesion score | Incidence of adhesion (%) | Note |
| --- | --- | --- | --- |
| 24 | 0.5 | 25 | Ex. 13 |
| 25 | 0.6 | 33 | Ex. 16 |
| 26 | 0.4 | 16 | Ex. 19 |
| 27 | 1.2 | 45 | Seprafilm |
| 28 | 1.6 | 88 | Control |

As evident from Table 4, an adhesion preventive effect of the carboxymethyl cellulose having been made hardly soluble in water of the present invention was found, relative to the adhesion score 1.6 of the control.

EXAMPLE 21

Test on Wound Treating Effect by Means of a Rat Apellous Model

The hair at the back of a Wister male rat of 7 weeks old (about 200 g) was shaved, and by means of ophthalmic scissors, the back skin portion was taken off in a circle shape with a diameter of 2 cm under anesthesia with ether, to prepare a complete apellous wound. A non-treated group having only medical non-woven gauzes (40×40 mm: double layered) applied, and treated groups having the sheet or film (30×30 mm) prepared in each of Examples 1, 9, 15, 17 and 19 and Comparative Example 2 covered on the wound surface and having medical non-woven gauzes (40×40 mm: double layered) applied, were set. Six rats were used for each group. The medical non-woven gauzes were set by an adhesive dressing and further fixed by taping.

The curing effects were compared by measuring the change with time of the wound area. Namely, the area ratio to the initial wound area is obtained by the following formula, and its change in time was examined. The results are shown in Table 5.

Area ratio (%)={(long diameter×short diameter of the wound area on the inspection day)/(long diameter×short diameter of the initial wound area)}×100

TABLE 5

| Test No. | Area ratio (%) | | | | | Note |
| --- | --- | --- | --- | --- | --- | --- |
| | 0 day | 2 days | 3 days | 7 days | 10 days | |
| 29 | 100 | 90 | 78 | 53 | 42 | Ex. 1 |
| 30 | 100 | 85 | 74 | 49 | 37 | Ex. 9 |
| 31 | 100 | 85 | 72 | 40 | 31 | Ex. 15 |
| 32 | 100 | 88 | 76 | 39 | 34 | Ex. 19 |
| 33 | 100 | 91 | 80 | 62 | 55 | Comp. Ex. 2 |
| 34 | 100 | 92 | 83 | 69 | 61 | Control |

As evident from Table 5, it was confirmed that the change in time was significant with respect to the carboxymethyl cellulose having been made hardly soluble in water of the present invention as compared with the change with time of the area ratio of the control, and a wound treating effect was confirmed. Here, the change in the area ratio by the sponge of the carboxymethyl cellulose obtained in Comparative Example 2 was slightly larger than the control, however, it was small as compared with the change by the carboxymethyl cellulose having been made hardly soluble in water, and the wound treating effect is considered to be small.

EXAMPLE 22

The carboxymethyl cellulose having been made hardly soluble in water obtained in Example 15 was freeze-dried to obtain a sheet containing 5.0 mg/cm$^2$.

EXAMPLE 23

Physiological saline was added to the carboxymethyl cellulose having been made hardly soluble in water obtained in Example 15 so that the carboxymethyl cellulose concentration became 1 mass %, and crushing by means of a microhomogenizer (NISSEI EXCEL AUTO HOMOGENIZAER) was carried out to obtain a slurry containing about 3 mass % of the carboxymethyl cellulose having been made hardly soluble in water.

EXAMPLE 24

Bone Repair of the Carboxymethyl Cellulose having been made Hardly Soluble in Water by Means of a Rabbit Skull Bone Defective Model The carboxymethyl celluloses having been made hardly soluble in water in a form of a sheet (diameter 1 cm, height 3 mm) and in a form of a slurry obtained in Examples 22 and 23, respectively, were subjected to the following test. Further, as a control, a non-treated group having only physiological saline applied thereto was set.

Curative Effect Test

15 Japanese White rabbits (about 2.5 kg) were divided into three groups, each consisting of five rabbits, and a group for application of the carboxymethyl cellulose having been made hardly soluble in water in a form of a sheet of Example 22, a group for application of the slurry of Example 23 and a non-treated group were set. Embedding was carried out in such a manner that the hair at the head of each rabbit was shaved, and a bone defective portion (diameter 5 mm) was formed on the skull bone by means of a microdrill under anesthesia with ether, and the carboxymethyl cellulose having been made hardly soluble in water was filled in the bone defective portion, followed by suturing.

Nine weeks after the embedding, rabbits having a hardly soluble hyaluronic acid embedded and rabbits having a freeze-dried hyaluronic acid embedded were butchered, and their heads were dissected to observe the state at the embedded portion, and one having the bone defective portion (diameter 5 mm) repaired and the skull bone connected was judged to be repaired. The remaining ratio of the carboxymethyl cellulose having been made hardly soluble in water was calculated based on the embedded carboxymethyl cellulose in the rabbit, and the state at the embedded portion was observed together. The results are shown in Table 6.

TABLE 6

| Test No. | Ratio of bone repair | Note |
| --- | --- | --- |
| 35 | 4/5 | Ex. 22 |
| 36 | 4/5 | Ex. 23 |
| 37 | 1/5 | Non-treated group |

As evident from Table 6, every rabbit grew normally. However, with respect to the state of the tissue, slight inflammation in the tissue was observed in the non-treated group, whereas no abnormality was observed on the tissue state at the embedded portion with respect to the carboxymethyl cellulose having been made hardly soluble in water. Further, in the group for application of the carboxymethyl cellulose having been made hardly soluble in water, acceleration of bone repair was confirmed.

EXAMPLE 25

The carboxymethyl cellulose used in Example 1 and chondroitin-6-sulfate having a molecular weight of about $3.5 \times 10^4$ Da (manufactured by Seikagaku Corporation) were dissolved in distilled water so that each become 0.5 mass %. The pH of the prepared aqueous solution was adjusted with 1N nitric acid to pH 1.5. 15 ml of the acidic aqueous solution was put into a polystyrene container of 30 ml and placed in a freezer set at −20° C. It was left to stand for 5 days, and then thawed at 25° C. Then, neutralization was carried out with water and a phosphate buffer having a concentration of 100 mM (pH 6.8) to obtain a spongy carboxymethyl cellulose composition having been made hardly soluble in water.

EXAMPLE 26

The carboxymethyl cellulose used in Example 10 and polyvinyl alcohol (polymerization degree: 1,500, manufactured by Wako Pure Chemical Industries, Ltd.) were dissolved in distilled water so that they were 0.5 mass % and 10 mass %, respectively. The pH of the prepared aqueous solution was adjusted with 1N nitric acid to pH 1.5. 15 ml of the acidic aqueous solution was put into a polystyrene container of 30 ml and placed in a freezer set at −20° C. It was left to stand for 5 days, and then thawed at 25° C. Then, neutralization was carried out with water and a phosphate buffer having a concentration of 100 mM (pH 6.8) to obtain a spongy carboxymethyl cellulose composition having been made hardly soluble in water.

EXAMPLE 27

The carboxymethyl cellulose used in Example 10 and sodium alginate (manufactured by Funakoshi K. K.) were dissolved in distilled water so that each became 0.5 mass %. The pH of the prepared aqueous solution was adjusted with 1N nitric acid to pH 1.5. 15 ml of the acidic aqueous solution was put into a polystyrene container of 30 ml and placed in a freezer set at −20° C. It was left to stand for 7 days, and then thawed at 25° C. Then, neutralization was carried out with water and a phosphate buffer having a concentration of 100 mM (pH 6.8) to obtain a spongy carboxymethyl cellulose composition having been made hardly soluble in water.

EXAMPLE 28

The carboxymethyl cellulose used in Example 10 and chitosan (manufactured by Wako Pure Chemical Industries, Ltd.) were dissolved in distilled water so that they were 1.0 mass % and 0.1 mass %, respectively. The pH of the prepared aqueous solution was adjusted with 1N nitric acid to pH 1.5. 15 ml of the acidic aqueous solution was put into a polystyrene container of 30 ml and placed in a freezer set at −20° C. It was left to stand for 5 days, and then thawed at 25° C. Then, neutralization was carried out with water and a phosphate buffer having a concentration of 100 mM (pH 6.8) to obtain a spongy carboxymethyl cellulose composition having been made hardly soluble in water.

EXAMPLE 29

Test on Cytotoxicity of the Carboxymethyl Cellulose having been made Hardly Soluble in Water A test on cytotoxicity was carried out with respect to the carboxymethyl celluloses having been made hardly soluble in water obtained in Examples 1 to 6, 9, 11 and 14 to 17 and the carboxymethyl cellulose compositions having been made hardly soluble in water obtained in examples 25 to 28.

The cytotoxicity of the carboxymethyl cellulose having been made hardly soluble in water obtained according to the present invention was evaluated by observing the proliferation behavior of a normal human skin-derived fibroblast culture in the presence of the carboxymethyl cellulose having been made hardly soluble in water obtained according to the present invention without contact between them. A prepared product was immersed in a phosphate-buffered physiological saline and then freeze-dried. The freeze-dried product was mechanically pulverized, and 20 mg of the pulverized product was loaded on a cell culture insert (pore size: 3 μm) manufactured by Falcon and immersed in the cell culture. For a control experiment, incubation was carried out in the absence of the carboxymethyl cellulose having been made hardly soluble in water.

Incubation conditions Plate: 12-well plate for cell culture
    Medium: DMEM medium+10% fetal bovine serum, 2 ml/well
    Temperature: 37° C. (under 5% $CO_2$)
    Cell number: $1 \times 10^4$ cells/well After 2, 5 and 8 days of incubation, the cell culture was examined on the cell density under an inverted microscope. As a result, it was found that the cell culture had grown in the presence of the carboxymethyl cellulose having been made hardly soluble in water as satisfactorily as that in the control experiment, and thereby it was ascertained that the carboxymethyl cellulose having been made hardly soluble in water and its composition obtained according to the present invention had no cytotoxicity.

INDUSTRIAL APPLICABILITY

As described in the foregoing, according to the present invention, a soluble cellulose derivative having been made hardly soluble in water comprising a soluble cellulose derivative, can be prepared simply without using any chemical cross-linking agent or chemical modifying agent. Adverse effects over biocompatibility resulting from use of a chemical cross-linking agent or chemical modifying agent can be avoided. Further, since the solubility can easily be controlled, it is useful for medical materials.

The invention claimed is:

1. A tissue-covering medical material which comprises a carboxy-cellulose derivative, wherein said derivative is prepared by a process, which comprises:
    dissolving a carboxy-cellulose derivative in water to provide an aqueous solution;
    acidifying the aqueous solution of the carboxy-cellulose derivative to a pH no greater than 2.0; and
    freezing and thawing the acidic aqueous solution of the carboxy-cellulose derivative,
    wherein the carboxy-cellulose derivative has a molecular weight that ranges from 10-500 kd, and
    wherein the tissue-covering medical material does not contain a polyethylene glycol.

2. A tissue-covering medical material according to claim 1, wherein the carboxy-cellulose derivative is substantially unmodified with a chemical crosslinking agent or a chemical modifying agent.

3. A tissue-covering medical material according to claim 1, wherein the concentration of the carboxy-cellulose derivative is at least 5 mass %.

4. A tissue-covering medical material according to claim 1, wherein said process further comprises:
    storing the acidified aqueous carboxy-cellulose derivative solution prior to freezing.

5. A tissue-covering medical material according to claim 1, wherein said process further comprises:
    storing the acidified aqueous carboxy-cellulose derivative solution.

6. A tissue-covering medical material according to claim 1, wherein said process further comprises:
    adding a polar organic solvent to the acidified aqueous solution.

7. A tissue-covering medical material according to claim 1, wherein the acidifying occurs by contacting the aqueous carboxy-cellulose derivative solution with a cation exchange resin.

8. A tissue-covering medical material according to claim 1, wherein said process further comprises:
    concentrating the acidified aqueous carboxy-cellulose derivative solution.

9. A tissue-covering medical material according to claim 1, wherein the carboxy-cellulose derivative has a fibrous structure or a film-form structure.

10. A tissue-covering medical material according to claim 2, wherein the carboxy-cellulose derivative has a fibrous structure or a film-form structure.

11. A tissue-covering medical material according to claim 1, wherein the percentage dissolution of the carboxy-cellulose derivative is at most 50% in 3 hours in a neutral aqueous solution at 60° C.

12. A tissue-covering medical material according to claim 1, wherein the carboxy-cellulose derivative is carboxymethyl cellulose.

13. A tissue-covering medical material according to claim 1, which does not contain hyaluronic acid or hyaluronates.

14. A tissue-covering medical material according to claim 1, which consists of the carboxy-cellulose derivative.

* * * * *